US009911357B2

(12) United States Patent
Rytky et al.

(10) Patent No.: US 9,911,357 B2
(45) Date of Patent: Mar. 6, 2018

(54) TRAINING GUIDANCE APPARATUS

(75) Inventors: Pekka Rytky, Oulu (FI); Mika Erkkilä, Oulu (FI)

(73) Assignee: POLAR ELECTRO OY, Kempele (FI)

( * ) Notice: Subject to any disclaimer, the term of this patent is extended or adjusted under 35 U.S.C. 154(b) by 435 days.

(21) Appl. No.: 13/557,321

(22) Filed: Jul. 25, 2012

(65) Prior Publication Data

US 2013/0040271 A1 Feb. 14, 2013

(30) Foreign Application Priority Data

Aug. 10, 2011 (FI) ...................................... 20115791

(51) Int. Cl.
G09B 19/00 (2006.01)
A63B 69/00 (2006.01)
G06F 19/00 (2018.01)

(52) U.S. Cl.
CPC ..... *G09B 19/0038* (2013.01); *G06F 19/3481* (2013.01)

(58) Field of Classification Search
CPC ...................................................... G09B 19/00
USPC ........................................................ 434/247
See application file for complete search history.

(56) References Cited

U.S. PATENT DOCUMENTS

| 6,430,997 | B1 * | 8/2002 | French | A63B 24/0003 |
| | | | | 73/379.04 |
| 6,672,991 | B2 * | 1/2004 | O'Malley | A63B 24/0075 |
| | | | | 482/1 |
| 7,166,062 | B1 * | 1/2007 | Watterson | A63B 22/00 |
| | | | | 482/1 |
| 8,066,514 | B2 * | 11/2011 | Clarke | A63B 24/00 |
| | | | | 434/236 |
| 2006/0229161 | A1 * | 10/2006 | Demas | A63B 24/00 |
| | | | | 482/1 |
| 2007/0074618 | A1 | 4/2007 | Vergo | |
| 2008/0141135 | A1 * | 6/2008 | Mason | G11B 27/034 |
| | | | | 715/719 |
| 2009/0049979 | A1 | 2/2009 | Naik et al. | |
| 2009/0075782 | A1 * | 3/2009 | Joubert | A63B 24/0075 |
| | | | | 482/9 |
| 2010/0035726 | A1 | 2/2010 | Fisher et al. | |
| 2010/0292599 | A1 * | 11/2010 | Oleson | A63B 24/0062 |
| | | | | 600/519 |

(Continued)

FOREIGN PATENT DOCUMENTS

WO WO2010063884 A1 6/2010
WO WO2011008571 A1 1/2011

OTHER PUBLICATIONS

Tuomo Reiniaho, Finnish Search Report for corresponding Finnish Application No. 20115791, p. 1, dated Mar. 15, 2012.

*Primary Examiner* — Thomas Hong
(74) *Attorney, Agent, or Firm* — Hoffmann & Baron, LLP

(57) ABSTRACT

A solution for training guidance is provided. A method related to the solution includes acquiring, in a training guidance apparatus, cardiovascular data representing cardiovascular measurement on a user carrying out a physical exercise, wherein the acquired cardiovascular data is real-time data measured during the physical exercise. The method further includes determining exercise guidance attributes from the cardiovascular data with respect to at least one training target of the physical exercise, selecting a video clip matching with the guidance attributes, and causing display of the video clip to the user.

23 Claims, 3 Drawing Sheets

(56) References Cited

U.S. PATENT DOCUMENTS

2011/0319229 A1* 12/2011 Corbalis ............ A63B 71/0622
                                                         482/9
2014/0038778 A1*  2/2014 Baudhuin ........................ 482/8
2015/0216427 A1*  8/2015 Granqvist ............ A61B 5/0006
                                                         600/483

* cited by examiner

| VIDEO FILE | META DATA (ATTRIBUTES) |
|---|---|
| 502 VIDEO TITLE 1 | 504 START EXERCISE |
| 506 VIDEO TITLE 2 | 508 STOP EXERCISE |
| 510 VIDEO TITLE 3 | 512 INCREASE INTENSITY |
| 514 VIDEO TITLE 4 | 516 WARMUP TRAINING |

TRAINING GUIDANCE APPARATUS

CROSS-REFERENCE TO RELATED APPLICATION

This application claims priority based on Finnish Application No. 20115791, filed Aug. 10, 2011, which is incorporated herein by reference in its entirety.

BACKGROUND

Field

The invention relates to the field of physical training systems and, particularly, to an arrangement for guiding a user during a physical exercise.

Description of the Related Art

Physical training may be carried out indoors at home or at a gym. At the gym, there may be provided a professional instructor with whom a personal training program may be designed. At home, such a training instructor is not typically available. Some exercise apparatuses such as treadmills and/or exercise cycles may include preconfigured training programs that control a resistance or exertion during the exercise. Such programs affect the real exertion during the exercise indirectly, and they cannot affect or instruct the user to reach a desired exertion level, as different users may respond differently to the increased resistance.

SUMMARY

According to an aspect of the present invention, there is provided a method comprising: acquiring, in a training guidance apparatus, cardiovascular data representing cardiovascular measurement on a user carrying out a physical exercise, wherein the acquired cardiovascular data is real-time data measured during the physical exercise; determining exercise guidance attributes from said cardiovascular data with respect to at least one training target of the physical exercise; selecting a video clip matching with the guidance attributes; and causing display of said video clip to the user.

According to yet another aspect of the present invention, there is provided a computer program product embodied on a non-transitory distribution medium readable by a computer and comprising program instructions which, when loaded into an apparatus, execute a computer process comprising: acquiring, in a training guidance apparatus, cardiovascular data representing cardiovascular measurement on a user carrying out a physical exercise, wherein the acquired cardiovascular data is real-time data measured during the physical exercise; determining exercise guidance attributes from said cardiovascular data with respect to at least one training target of the physical exercise; selecting a video clip matching with the guidance attributes; and causing display of said video clip to the user.

According to another aspect of the present invention, there is provided an apparatus comprising at least one memory storing computer program code; and at least one processing circuitry, wherein the processing circuitry, together with the at least one memory and the computer program code, is configured to cause the apparatus to acquire cardiovascular data representing cardiovascular measurement on a user carrying out a physical exercise, wherein the acquired cardiovascular data is real-time data measured during the physical exercise, to determine exercise guidance attributes from said cardiovascular data with respect to at least one training target of the physical exercise, to select a video clip matching with the determined guidance attributes, and to cause display of said video clip to the user.

According to yet another aspect, there is provided a system comprising: a heart rate transmitter configured to acquire cardiovascular data representing cardiovascular measurement on a user carrying out a physical exercise, wherein the acquired cardiovascular data is real-time data measured during the physical exercise; a storage configured to store a plurality of video clips, each video clip associated metadata comprising exercise guidance attributes; and an apparatus, comprising at least one memory storing computer program code and at least one processing circuitry, wherein the processing circuitry, together with the at least one memory and the computer program code, is configured to cause the apparatus to acquire the cardiovascular data from the heart rate transmitter, to determine exercise guidance attributes from said cardiovascular data with respect to at least one training target of the physical exercise, to select a video clip matching with the determined guidance attributes, and to cause display of said video clip to the user.

In an embodiment, the apparatus is configured to provide a plurality of video clips, wherein each video clip is associated with metadata comprising guidance attributes. In an embodiment, the video clips are stored as video files in a standard video format.

In an embodiment, a processing circuitry of the apparatus is configured to communicate over a logical connection with an exercise measurement device worn by the user and configured to measure cardiovascular data from the user, wherein the cardiovascular data is streamed from the exercise measurement device to the apparatus over the logical connection. In an embodiment, the logical connection is a network layer or a transport layer connection. In an embodiment, the apparatus is configured to connect the logical connection through a public network between the apparatus and the exercise measurement device.

In an embodiment, the processing circuitry is configured to determine a training program comprising a plurality of training phases, each training phase associated with a video clip, wherein a plurality of video clips associated with said plurality of training phases are arranged in a determined order for display, to provide training target parameters for each phase, to monitor said acquired cardiovascular data in relation to the training target parameters during each phase, upon determining on the basis of said monitoring a need to instruct the user, to determine exercise guidance attributes describing the needed instruction, to select an interrupt video clip matching with the determined exercise guidance attributes describing the needed instruction, and to cause interruption during the display of a video clip associated with current training phase and displaying the interrupt video clip during the interruption.

Further embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
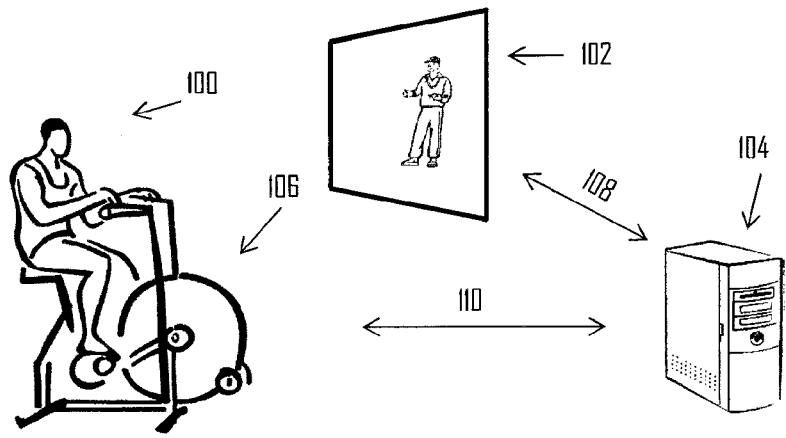
FIG. 1 illustrates an exercise arrangement to which embodiments of the invention may be applied.

FIG. 1 illustrates an exemplary scenario to which embodiments of the invention may be applied. Referring to FIG. 1, a user 100 is carrying out a physical exercise in the form of a cycling exercise, wherein the user operates an exercise bicycle 106. The user 100 may wear an exercise measurement system configured to measure exercise-related physiological data from the user 100 non-invasively. Such an exercise measurement system may comprise a cardiovascular measurement system which measures user's cardiovascular data from the user's body. In an embodiment, the cardiovascular data is measured by applying a skin contact from the chest, wrist, or other human parts. In some embodiments, the exercise measurement system is included in the exercise bicycle 106. The exercise measurement system may be configured to transmit the measured physiological data to a server 104 which may be a computer (PC) over a connection 110. The server 104 may store a training program for the exercise currently carried out by the user 100, and the server 104 may utilize the received physiological data so as to determine whether or not the user 100 follows the training program. The server 104 may control a display unit 102 in the vicinity of the user 100 to display appropriate training guidance video clips, and the server 104 may select the video clips to be displayed on the basis of the received physiological data and the training program, as will be described in greater detail below. In other words, the server 104 executes a training guidance algorithm that interactively guides the user through visual or audio-visual video output through the display unit 102 over a connection 108. The training guidance algorithm maps the received physiological data to the training program so as to determine whether or not there is need to instruct the user 100 to change the current phase of the exercise. As a consequence, improved training experience is achieved through the versatility of audio-visual instruction means provided by the selection of the appropriate video clips. Furthermore, improved training results are achieved, as specific instructions may be provided to the user.

The physiological data may be selected from a group comprising cardiovascular data, body temperature, power output, body motion data characterizing motion of the person's body, energy expenditure data and training load data. The training load refers to the load to the human metabolic system due to an exercise. The training load can be determined from cardiovascular data and/or motion data according to a state-of-the-art algorithm.

Figure 2:
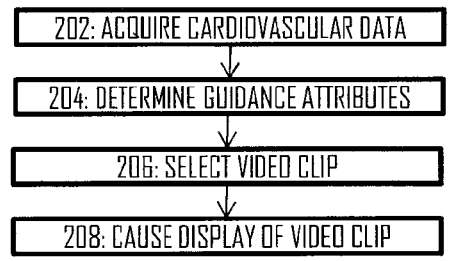
FIG. 2 illustrates a flow diagram of a training guidance process according to an embodiment of the invention.

FIG. 2 illustrates a flow diagram of the training guidance algorithm. The algorithm may be executed as a computer program in a training guidance apparatus which may be comprised in the server 104. The server 104 may be a local server such as a PC or a video console, or it may be a network server accessible through at least one network, e.g. the Internet. The at least one network may comprise at least one public network. In some embodiments, the local server may be maintained at a gym or home, and the local server may be reached over a wireless connection, e.g. IEEE 802.11 connection (Wi-Fi). Referring to FIG. 2, cardiovascular data representing cardiovascular properties of the user 100 are acquired in block 202. The training guidance apparatus determines in block 204 exercise guidance attributes from said cardiovascular data with respect to at least one training target of the physical exercise. Thereafter in block 206, a video clip matching with the guidance attributes is selected. In block 208 the training guidance apparatus causes display of said video clip to the user.

In an embodiment, the cardiovascular data is at least one of the following: heart rate, heart rate beat-to-beat intervals, heart rate variability, breathing frequency, and an electrocardiographic signal.

Instead of using cardiovascular data, or in addition to using the cardiovascular data, any other physiological data may be acquired in block 202 and used in any embodiment described herein. Other embodiments of the physiological data are listed above.

In an embodiment, the video clip is stored as a video file encoded according to a standard video encoding format, e.g. MPEG (Moving Picture Experts Group), AVI (Audio Video Interleave), ASF (Advanced Streaming Format), and VOB (Video Object).

Figure 3:
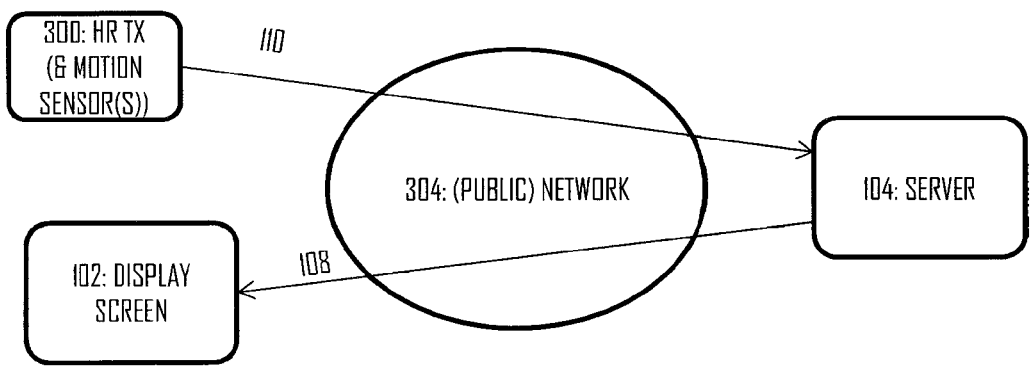
FIG. 3 illustrates connections between apparatuses in a system according to an embodiment of the invention.

An embodiment of the operation of the training guidance algorithm is described in greater detail below with reference to FIG. 4 but, before that, let us consider an embodiment of interconnections 108, 110 between the server 104 and the other parts of the training guidance system with reference to FIG. 3. Referring to FIG. 3, the server 104 may be connected to the exercise measurement system 300 and the display unit 102 through at least one public network 304. The public network 304 may be the Internet, for example.

In an embodiment, the exercise measurement system 300 comprises an exercise measurement device which may be a heart rate transmitter attached to the user's body, e.g. the chest. The exercise measurement system 300 may comprise a component attached to the user's skin, e.g. the heart rate transmitter. In another embodiment, the exercise measurement system 300 comprises a component attached to an exercise device, e.g. the exercise bicycle. In an embodiment, the exercise measurement system further comprises at least one motion sensor attached to the user 100. The sensor(s) may be attached to the user's 100 hand(s), foot/feet, head, and/or torso. The number of such motion sensor may be 1, 2, 3, 4, or 5, for example. The motion sensor may comprise one or more acceleration sensors to measure the motion. In an embodiment, the connection 110 between the server 104 and the heart rate transmitter and/or the motions sensor(s) comprises network layer or a transport layer connection or, in general, a connection on a higher layer than a link layer in an Open Systems Interconnection (OSI) model. The connection may be a transport control protocol (TCP)/Internet protocol (IP) connection, or a user datagram protocol (UDP) connection. The connection as defined herein should be interpreted broadly, as IP connection, for example, is generally considered as a connectionless communication service. As a consequence, the heart rate transmitter may have a dedicated IP address.

In an embodiment, the connection 110 is routed through at least one wireless connection, e.g. WiFi, Bluetooth, Bluetooth Low Energy, and Zigbee, and through at least one wired connection, e.g. Ethernet. For example, the wireless connection may be provided between the heart rate transmitter and a wireless access point, while the wired connection may be provided between the access point and the server 104. Additionally, the connection may comprise internal signal routes in the heart rate transmitter, the access point, and the server 104.

In an embodiment, the measured physiological data is streamed from the heart rate transmitter or a similar measurement apparatus to the server. Streaming may comprise providing the measured physiological data in real-time during the exercise. The physiological data may be measured continuously or repeatedly during the exercise, and the measurement results may be transmitted to the server immediately after each measurement. In an embodiment, the measured physiological data is transmitted from the measurement apparatus directly to the public network. In another embodiment, the measured physiological data is first transmitted to a user interface apparatus, e.g. a wrist unit, a palm device, or a mobile communication apparatus (mobile phone), and the physiological data is then routed from the user interface apparatus to the public network. As a consequence, the user interface apparatus may process the measured data, display it to the user, and forward the data to the server 104.

In an embodiment, the display unit 102 is a high resolution display screen, e.g. high definition (HD) resolution with 720 or 1080 vertical pixels. The display unit 102 may be a monitor or television screen, or it may be a video projector. The connection 108 between the server 104 and the display unit may comprise at least one of the following connections: high-definition multimedia interface (HDMI), digital video interface (DVI), Wi-Fi connection. The connection 108 may comply with digital living network alliance (DLNA) requirements. As a consequence, the server 104 may be understood as a media server provided with the training guidance algorithm according to embodiments of the invention.

In an embodiment, the connections 108, 110 are routed at least partially through the same network 304, e.g. the Internet. In another embodiment, the connections 108, 110 are routed through partially or even completely different networks, e.g. the connection 110 is routed through a Bluetooth network between the server 104 and the heart rate transmitter, while connection 108 is routed through a WiFi network between the server and the display unit 102.

Figures 4, 5:
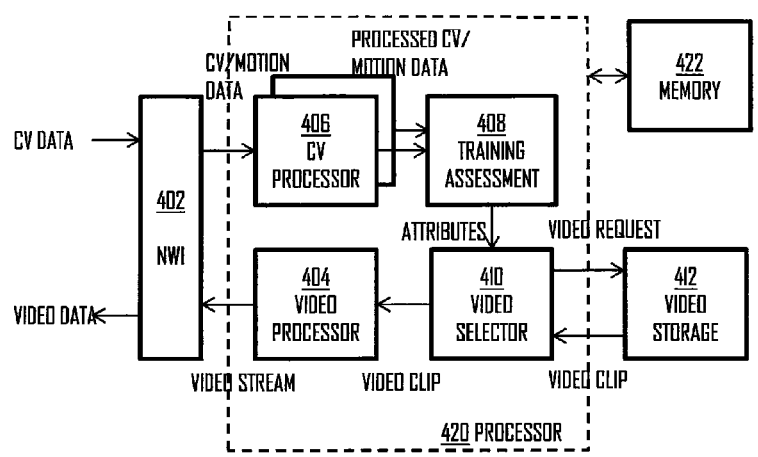
FIG. 4 illustrates a functional block diagram of a training guidance apparatus according to an embodiment of the invention.
FIGS. 5 and 6 illustrate embodiments of databases used for selecting a video clip for use in training guidance according to an embodiment of the invention.

Let us now consider the structure of the server 104 and the operation of the training guidance algorithm in greater detail with reference to FIG. 4. FIG. 4 illustrates a functional block diagram illustrating modules comprised in the server 104. The server 104 may comprise at least one memory 422 and at least one processor 420, wherein the at least one memory 422 stores computer programs configuring the at least one processor 420 to execute the training guidance algorithm according to FIG. 2. As a consequence, the at least one processor 420 and the at least one memory with the computer program form an embodiment of processing means for carrying out the method of FIG. 2. The memory 422 may be realized by at least one random access memory (RAM) chip, but the memory 422 may also comprise non-volatile memory resources, e.g. flash memory. The server 104 may further comprise a video storage 412 realized by a non-volatile memory storage, e.g. a hard drive, an optical or magnetic storage medium, and/or a flash chip. The server 104 may further comprise a network interface adapter 402 providing the server with a connection to the display unit 102 and the exercise measurement system 300. The network interface adapter 402 may provide the server 104 with an Ethernet connection, a digital subscriber line (xDSL) connection, a wireless connection through Wi-Fi, for example. In general, the network interface adapter may provide the server 104 with a communication connection with external devices.

With respect to the operation of the training guidance algorithm, the server 104 receives through the network interface adapter 402 cardiovascular (CV) data. Examples of the CV data are listed above. In the server, the CV data is first processed by a CV processor module 406 configured to convert the CV data into an appropriate format. For example, if the received CV data comprises the beat-to-beat intervals, the CV processor 406 may convert the beat-to-beat intervals into heart rate and/or heart rate variability values. Alternatively, or additionally, the CV processor module 406 may be configured to derive additional CV data from the received CV data. Such additional CV data may comprise momentary energy expenditure or training load, for example. The CV processor module outputs processed CV data, wherein the processed CV data may comprise the converted CV data and the additional CV data.

In some embodiments, the exercise measurement system 300 provides all the necessary data in a suitable format and, thus, the CV processor module 406 may be bypassed or even completely omitted.

In the embodiments of the exercise measurement system utilizing the motion sensor(s), the network interface adapter 402 is further configured to receive the motion data, and the motion data may be processed by a motion data processor module (not shown) configured to convert the received motion data into an appropriate format. The motion data processor module may be understood as a component that is operationally similar to the CV processor module 406. The difference is that the motion data processor module processes the motion data.

The processed CV data and, optionally, the motion data is then applied to a training assessment module 408. The training assessment module 408 may be initiated at the beginning of the exercise with a training program to be carried out.

The training program may be considered as a plan for an exercise or a series of exercises. The training program is defined by training program parameters. The training program parameters may define one or more of the following features of the training program: duration of at least one exercise; at least one phase of the at least one exercise, order of a plurality of phases comprised in an exercise, and duration of each phase. The phases may comprise at least one of the following: warm-up, fundamental phase of the exercise, cool down training, stretching training, muscle training, fat burn training, fitness training, maximum performance training, interval training, relaxation training, fitness test, and rhythmic training such as dance. The duration of the exercise may define the total duration for a single exercise or, if the training program comprises a plurality of exercises, the duration may comprise duration values for a plurality of exercises comprised in the training program.

In an embodiment, the training program is defined by the user. In another embodiment, the training assessment module 408 is configured to design the training program according to user preferences. The training assessment module may design the training program by taking into account the user's previous training history so as to match the training program with the user's physiological state and fitness. There may be provided a ranking for the user, and the training assessment module 408 may be configured to select at least one of the training program, an exercise, and a displayed theme (see more about the themes below) of the exercise according to the ranking of the user.

Each phase, exercise, and/or whole training program may be provided with CV data targets. In an embodiment, the CV data target should be fulfilled before moving to the next phase and/or before completing the exercise or the training program. At least some of the phases may have a CV data profile defining, for example, target heart rate zones, heart rate limits for each heart rate zone, and optionally also target time intervals for each zone. Additionally, or alternatively, at least one of the following training targets may be applied to at least one phase, exercise, and training program: at least one energy expenditure target, a target for total duration of the exercise, target duration for each phase of the exercise, training load representing physical exertion of the exercise, and heart rate limits for heart rate variability for the exercise and/or for each phase, e.g. fat burning, fitness training. Other parameters defining the training profile are naturally possible.

As mentioned above, the training program may expand over multiple exercises. At least some of the exercises may be repeated periodically, e.g. an exercise schedule for one week that is repeated weekly. The training assessment module 408 receives the processed CV data from the CV processor module 406, and it may compute additional data from the received processed CV data, e.g. a total energy expenditure, energy expenditure during a current exercise phase, accumulated time at one or more heart rate zones during the current phase, a maximum heart rate, and heart rate variability. Naturally, if the CV processor module 406 has already computed at least some of these parameters, redundant recomputation by the training assessment module 408 may be bypassed. The training assessment module then compares the processed CV data and/or the additional data with the training program parameters, e.g. at least one training target, and creates a list comprising at least one guidance attribute related to as how the training should continue. In an embodiment, the guidance attributes thus comprise at least one of the following: increase training intensity, decrease training intensity, increase/decrease training intensity gradually, show target heart rate. Additionally, the training assessment module may output the guidance attributes in connection with starting a new phase or ending a phase during the exercise. In an embodiment, the guidance attributes thus comprise at least one of the following: start exercise, stop exercise, start the next phase and an identifier of the next phase (examples of phases listed above). As the training assessment 408 module controls the phases of the exercise and the training program, it may be configured to deviate from the original training program by changing the exercise on-the-fly. For example, if the CV data shows that the user is exhausted during the exercise, it may skip at least one coming exercise phase by simply omitting command to enter the exercise phase and, instead, commanding the execution of a subsequent exercise phase. Instead of skipping one or more of the exercise phase, the training assessment module 408 may change the video clip of at least one exercise phase during the exercise on-the-fly, e.g. on the basis of the received CV data and/or the motion data.

With respect to the motion data, the training assessment module may determine some of the guidance attributes from the motion data. For example, an exercise phase may comprise a sequence of sub-phases, wherein each sub-phase is associated with a motion sequence, e.g. push ups, situ ups, hands up-and-down motion. Upon reception of a determined sequence of motion data, the training assessment module 408 may output a guidance attribute "start next sub-phase". In general, the training assessment module 408 may control the execution of the exercise in response to the received sequence of motion data by causing display of determined video clips in response to the received motion data.

The guidance attributes are output to a video selector module 410 configured to select an appropriate video clip from the video storage 412 on the basis of the received guidance attribute(s). Each video clip may be stored as a video file in the video storage 412. Each video file may be associated with meta data comprising said guidance attributes that define the video clip of the video file. FIG. 5 illustrates an embodiment of a database identifying a plurality of video files by titles or other identifiers 502, 506, 510, 514. Each video file is associated with a metadata information element 504, 508, 512, 516 describing the contents of the corresponding video file. For example, video file 502 is to be shown in connection with starting an exercise, as shown by the corresponding metadata 504, while video file 506 is to be shown in connection with ending an exercise. Meta data 512 defines that video file 510 contains instructions for the user to increase training intensity, while metadata 516 defines that video file 514 relates to a warm-up phase of the exercise.

Figure 6:
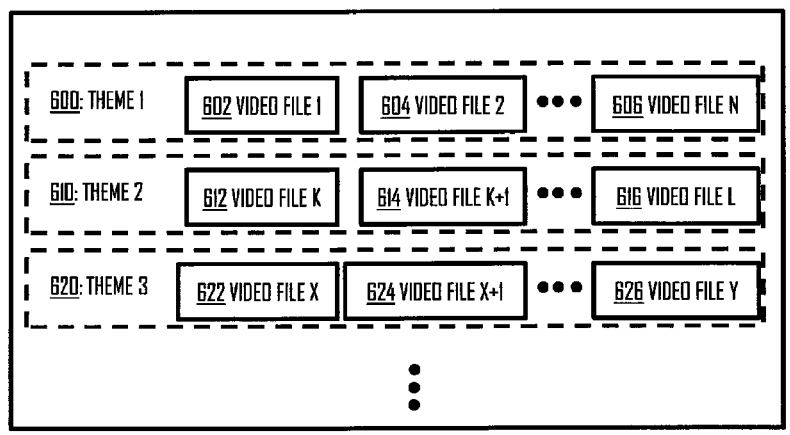

With the help of the metadata, the video selector module 410 fetches a video file providing a best match with the guidance attribute(s) received from the training assessment module 408. The video selector module 410 may store the database of FIG. 4 and determine the identifier of the video file to be fetched from the video storage 412. In an embodiment, the video clips or video files are each associated with a theme, and one of the themes may be selected for the exercise according to a user input, for example. Then, the exercise the video selector module 410 is configured to search for the video clip within video clips associated with the selected theme. The theme may be understood as a preference list of video clips displayable during the same exercise. FIG. 6 illustrates an embodiment of providing the video files with themes. The table of FIG. 6 may be comprised in the database of FIG. 5, or it may be a standalone table. The table of FIG. 6 may comprise groups 600, 610, 612, each group associated with a different theme, e.g. coaching video, interactive training video, animated training video, and character-based instructions video. Each group 600, 610, 620 may then comprise identifiers of those video files comprised in the group. For example, video files 602, 604, 606 belong to group 600, video files 612, 614, 616 belong to group 610, and video files 622, 624, 626 belong to group 620. As mentioned above, the embodiments of FIG. 5 and FIG. 6 may be combined. Thus, each video file element of FIG. 6 may comprise the title and the metadata of FIG. 5. For example, video file element 602 may comprise the video title element 502 and associated metadata element 504. The same logic applies to the other elements. Providing the themes 600, 610, 620 also reduces the number of video files the video selector module 410 searches for, thus reducing the computational cost.

At least some of the video clips may also comprise metadata that determines whether the video clip is a basic video clip or an interrupt video clip. For example, the basic video clips and their display sequence may be selected according to the planned training program beforehand or at the beginning of the exercise. The basic video clips may comprise video clips for the warm-up phase, fitness training phase, etc. The interrupt video clips are video clips that are used to instruct the user to follow the training program, and they may comprise video clips that instruct the user to change the current training behaviour, e.g. to increase the training intensity. The interrupt video clips may have priority over the basic video clips, which means that they interrupt the display of the basic video clips for the duration of the display of the interrupt video clip. Thereafter, the display of the interrupted basic video clip may be resumed.

Upon selecting the video file providing the best match with the guidance attribute(s), the video selector module 410 sends a video request comprising the identifier of the required video file to the video storage 412. When the video storage 412 is a hard drive or another media comprised in the server 104 or as a peripheral device of the server 104, the video selector module 410 may control directly the video storage to retrieve the video file from an appropriate memory location, thus carrying out the request. In an embodiment where the video storage is stored on an external server, for example, the video selector may send the request to such a server through the network interface adapter 402. In response to the request, the video selector module 410 receives the video file, and it outputs the video file to a video processor module 404. The video processor module 404 may be configured to decode the video file, e.g. by extracting the encoded video package according to a corresponding standard extraction process (MPEG, AVI, ASF). Then, the video processor module 404 may output a video data, e.g. a video stream, to the display unit 102 through the network interface adapter or through another display connection, e.g. HDMI. The video processor module 404 may function as a display adapter of the server 104, and it may control the display contents of the display unit 102 with respect to the displaying the video clip. The video processor module 404 may control the display unit to display the video clip on the whole display area of the display unit 102. When the resolution of the video clip does not match the native resolution of the display unit, the video processor module 404 or an internal video scaling circuitry of the display unit may scale the resolution of the video clip to match with the native resolution of the display unit 102.

In an embodiment, the display unit 412 stores the video clips, i.e. the display unit comprises the video storage. In such embodiments, the video processor 404 or the video selector module 410 may transmit to the display unit as the video data a command identifying the video file to be displayed.

Let us consider an example. Let us assume that the server 104 receives a training program from the user. As a consequence, the training assessment module 408 loads the appropriate training program schedule and associated training target(s) from the memory 422. Then, the server 104 receives a start instruction from the user 100 at the beginning of the exercise. This activates the training assessment module 408 to output a guidance attribute "start exercise", which serves as an input parameter for the video selector module 410 to fetch a video file related to starting an exercise. Then, the video selector module instructs the video processor 404 to cause the display of the video file through the display unit. Thereafter, or together with the "start exercise" training attribute, the training assessment module 408 may provide the video selector module 410 with a guidance attribute related to the first phase of the exercise, e.g. "warm-up training". This may trigger the training assessment module 408 to fetch target parameters for the warm-up training. Upon reception of the "warm-up training" attribute, the video selector module 410 fetches from the video storage 412 a warm-up training video clip and outputs the video clip to the video processor 404 that causes its display to the user 100. During the warm-up phase, the training assessment module 408 receives the CV data and monitors the CV data in relation to the target parameters. For example, the target parameters may comprise a heart rate upper limit which should not be exceeded during the warm-up phase. If the training assessment module 408 detects from the received CV data that the current heart rate of the user 100 exceeds the heart rate upper limit, the training assessment module 408 may output a guidance attribute "decrease training intensity" to the video selector module 410.

Upon reception of this guidance attribute, the video selector module 410 fetches a video clip instructing the user 100 to decrease the training intensity, and outputs the video clip to the video processor 404. This video clip may be the above-mentioned interrupt video clip, and upon reception of the video clip from the video selector module 410, the video processor may interrupt the display of the warm-up video clip for the display of the video clip instructing the user 100 to decrease intensity. In an embodiment, the video processor provides a blended display of both video clips simultaneously. For example, the interrupt video clip may be displayed according to picture-in-picture principles, wherein the interrupt video clip is displayed on a sub-screen covering only a portion of the display screen, e.g. less than a quarter of the display are of the display screen. Meanwhile, the basic video clip is displayed on the rest of the screen area. In another embodiment, the two video clips are displayed as blended to each other. Both video clips may be processed to have transparency such that the both video clips cover substantially the whole display area and their pixels are mixed together.

Upon a preset time limit for the warm-up phase has expired, upon reaching a preset energy expenditure target for the warm-up phase, and/or upon another event ending the warm-up phase, the training assessment module 408 outputs a guidance attribute identifying the start of a subsequent phase of the exercise, e.g. "fitness training". As a consequence, the video selector module 410 fetches a video clip matching with the identified guidance attribute and causes its display to the user 100. The training assessment module may then fetch new target parameters for the fitness training phase. The targets may comprise:

| Target Parameter | Target Value |
|---|---|
| Total duration | 60 min |
| Heart rate zone 1 & duration | 110 to 125 bpm (20 min) |
| Heart rate zone 2 & duration | 126 to 145 bpm (35 min) |
| Heart rate zone 3 & duration | 146 to 165 bpm (5 min) |
| Energy expenditure target | 800 kcal |

During the exercise, the video clip and the target parameters may be adapted to each other such that the training targets are generally reachable by following the instructions of the video clip. The training assessment module 408 constantly monitors the received CV data and compares the CV data with the target parameters. Let us assume that at a given stage of this phase the current status of is as follows:

| Parameter | Value |
| --- | --- |
| Duration | 50 min |
| Accumulated energy expenditure | 700 kcal |
| Accumulated time in zone 1 | 20 min |
| Accumulated time in zone 2 | 25 min |
| Accumulated time in zone 3 | 5 min |
| Current heart rate | 115 bpm |

The comparison between the current status and the target parameters indicates that the user 100 should increase the exercise intensity so that the heart rate is raised to zone 2. Thus, the training assessment module outputs a guidance attribute "increase intensity", and the video selector fetches and causes display of a corresponding video clip. Furthermore, the training assessment module may estimate a final heart rate that should be maintained for the remaining duration of this training phase so as to match with the energy expenditure target, i.e. to consume the remaining 100 kilocalories (kcal) during the 10 remaining minutes. The training assessment module 408 may estimate the final heart rate by using an energy expenditure algorithm which relates the energy expenditure rate with the heart rate. Such algorithms are known in the art and, thus detailed description is omitted. Let us assume that the final heart rate is 140 bpm (beats per minute). The training assessment module may then output a guidance attribute "target heart rate 140 bpm" together with the guidance attribute "increase intensity". As a consequence, the video selector module 410 may select a video file that provides a best match with both guidance attributes. For example, the video selector module may fetch a video file that instructs the user 100 to increase intensity and that displays the final heart rate on the display screen as the target heart rate. In another embodiment, the video selector module 410 may fetch two separate video files. For example, the video selector module 410 may fetch a video file instructing the user to increase intensity, and another video file that includes music or other content playing a rhythm that matches with the final heart rate. For example, video clips containing music may be associated with the metadata identifying the tempo of the music in beats per minute, for example. Then, the received guidance attribute "target heart rate X bpm" may be matched with a video clip having as the metadata tempo X bpm.

Upon reaching the target duration in each heart rate zone and/or reaching the target energy expenditure, the training assessment module 408 initiates a subsequent phase or ends the exercise.

In an embodiment, the training assessment module 408 is configured to assess accumulated training load with respect to a target training load accumulation over a plurality of exercises and adjust future exercises so as to follow the target training load accumulation. The target training load accumulation may be understood as a superposition of training loads of a series of exercises. The target training load accumulation may be defined as a weekly training load accumulation or a monthly training load accumulation, for example. Let us consider a scenario where the training assessment module 408 detects that after a previous exercise the accumulated training load is less than the target training load accumulation. Upon detection of such an event, the training assessment module 408 may add an extra phase to the next exercise, wherein the training load of the extra phase may correspond to at least some of the difference between the accumulated training load and the target raining load accumulation. Similarly, upon detection that the accumulated training load is higher than the target training load accumulation, the training assessment module may discard or modify at least one phase of the next exercise to cause less training load.

In an embodiment, a minimum target heart rate is provided. The minimum target heart rate may be global value which applies to all training phases where the heart rate is monitored. When the training assessment module 408 detects that the heart rate falls below the minimum target heart rate, the training assessment module 408 assumes that the user is taking a break. As a consequence, the training assessment module 408 outputs a guidance parameter "pause", which causes the video selector module 410 to output a pause command to the video processor 404. Alternatively, the video selector module 410 may fetch a pause video clip and cause display of said pause video clip. It should be appreciated that the minimum target heart rate may be lower than the lowest target heart rate of a training phase. Upon detecting that the user's 100 heart rate drops below the lowest target heart rate, the training assessment module 408 may output a guidance parameter "increase intensity", but upon detecting that the user's 100 heart rate further drops below the minimum target heart rate, the training assessment module 408 may output a guidance parameter "pause". Upon detecting that the user's 100 heart rate rises above the minimum target heart rate, the training assessment module 408 may output guidance attribute "resume" which causes the video selector module 410 to control the video processor 404 to resume the playback of the paused video clip.

In an embodiment, different target parameters are selected for different training phases. However, some target parameters may be global target parameters that apply to all training phases or to a plurality of training phases. It should be appreciated that while in several embodiments described herein the target parameters relate to the CV data, corresponding target parameter values may be easily derived for the other types of physiological data.

Figure 7:
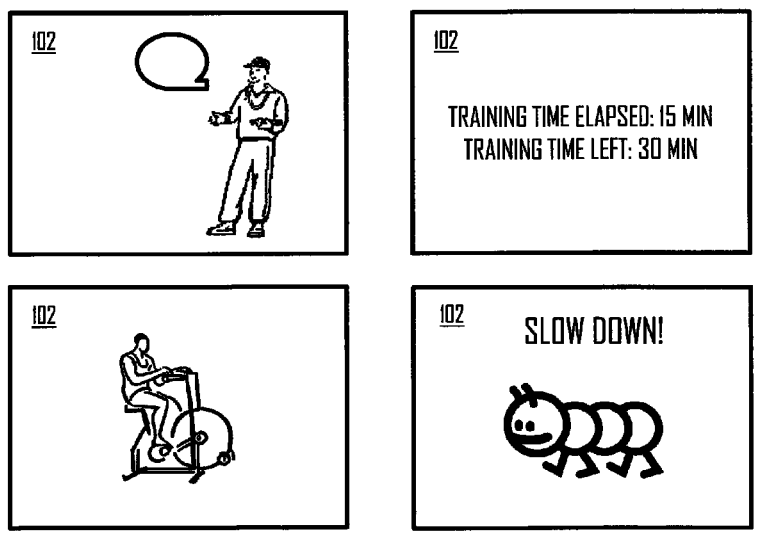
FIG. 7 illustrates embodiments of contents of video clips used training guidance according to an embodiment of the invention.

Let us now consider a few examples of video clips displayed to the user 100 on the display screen 102 with reference to FIG. 7. The video clips may comprise a video clip where a real person displayed on the video clip provides oral instructions (top left picture in FIG. 7), a video clip where audiovisual signals are provided, e.g. in a character form (top right picture in FIG. 7), a video clip where a real person carries out the same exercise (bottom left picture in FIG. 7) with a correct tempo/intensity that the user 100 should follow, and/or a video clip comprising animated characters and appropriate instructions (bottom right picture in FIG. 7). It should be appreciated that other types of video clips and themes may be provided, and the only limitation in the contents of the video clips with respect to the design is imagination of the designer.

At least some of the modules 406 to 410 may be realized by computer program modules executed by the processor 420 or, in general, a processing circuitry. The term 'circuitry' should be understood to refer to any one of the following: (a) hardware-only circuit implementations, such as implementations in only analog and/or digital circuitry, and (b) to combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) to circuits, such as a microprocessor(s) or a portion of a microprocessor(s), that require software or firmware for operation, even if the software or firmware is not physically present.

This definition of 'circuitry' applies to all uses of this term in this application. As a further example, as used in this application, the term "circuitry" would also cover an implementation of merely a processor (or multiple processors) or portion of a processor, e.g. one or more of a plurality of cores of the processor, and its (or their) accompanying software and/or firmware. The term "circuitry" would also cover, for example and if applicable to the particular element, an application-specific integrated circuit for the server 104.

The processes or methods described in connection with FIGS. 2 to 7 may also be carried out in the form of a computer process defined by a computer program. The computer program may be in source code form, object code form, or in some intermediate form, and it may be stored in some sort of carrier, which may be any entity or device capable of carrying the program. Such carriers include a record medium, computer memory, read-only memory, electrical carrier signal, telecommunications signal, and software distribution package, for example. Depending on the processing power needed, the computer program may be executed in a single electronic digital processing unit or it may be distributed amongst a number of processing units.

It will be obvious to a person skilled in the art that, as technology advances, the inventive concept can be implemented in various ways. The invention and its embodiments are not limited to the examples described above but may vary within the scope of the claims.

What is claimed is:

1. A method comprising: acquiring, in a training guidance apparatus by using a heart rate sensor device, cardiovascular data representing cardiovascular measurement on a user carrying out a physical exercise associated with a pre-defined cardiovascular training program of the physical exercise, wherein the acquired cardiovascular data is real-time data measured by the heart rate sensor device during the physical exercise, and wherein the cardiovascular training program is defined by a plurality of cardiovascular training targets for the physical exercise; determining, in the training guidance apparatus on the basis of the acquired cardiovascular data and at least one of the plurality of cardiovascular training targets, cardiovascular performance associated with the user with respect to the cardiovascular training program during the exercise; determining, on the basis of the cardiovascular performance with respect to the cardiovascular training program, training guidance attributes for the physical exercise; selecting a basic video clip matching with the training guidance attributes; causing display of said basic video clip to the user during the physical exercise; determining a need to instruct the user during said display of said basic video clip, and determining exercise guidance attributes describing the needed instruction; selecting an interrupt video clip matching with the determined exercise guidance attributes describing the needed instruction; causing interruption during the display of the basic video clip and displaying the interrupt video clip during the interruption; and upon determining, by the training guidance apparatus on the basis of the cardiovascular data with respect to the at least one of the plurality of cardiovascular training targets, that the user has fulfilled the at least one of the plurality of cardiovascular training targets, advancing the user to a next cardiovascular training target of the plurality of cardiovascular training targets different from the fulfilled at least one cardiovascular training target during the physical exercise, wherein the interruption during the display of the basic video clip causes the basic video clip and the interrupt video clip to be simultaneously displayed.

2. The method of claim 1, further comprising providing a plurality of basic video clips, wherein each video clip is associated with metadata comprising the training guidance attributes.

3. The method of claim 2, wherein the plurality of basic video clips is stored as video files in a standard video format.

4. The method of claim 1, further comprising:
providing a logical connection between the training guidance apparatus and an exercise measurement device worn by the user and configured to measure said cardiovascular data from the user; and
streaming said cardiovascular data from the exercise measurement device to the training guidance apparatus.

5. The method of claim 4, wherein the logical connection is a network layer or a transport layer connection.

6. The method of claim 4, wherein the logical connection is routed through a public network between the training guidance apparatus and the exercise measurement device.

7. The method of claim 1, further comprising:
determining the cardiovascular training program of the physical exercise comprising a plurality of training phases, each training phase associated with a basic video clip, wherein a plurality of basic video clips associated with said plurality of training phases are arranged in a determined order for display;
providing training target parameters for each phase;
monitoring said acquired cardiovascular data in relation to the training target parameters during each phase;
upon determining on the basis of said monitoring a need to instruct the user, determining exercise guidance attributes describing the needed instruction;
selecting the interrupt video clip matching with the determined exercise guidance attributes describing the needed instruction; and
causing interruption during the display of a basic video clip associated with current training phase and displaying the interrupt video clip during the interruption.

8. The method of claim 1, further comprising:
acquiring motion data of the user during the physical exercise of the user; and
determining the training guidance attributes from said cardiovascular data and motion data with respect to at least one cardiovascular training target of the physical exercise.

9. The method of claim 1, further comprising:
acquiring a new cardiovascular training target when the user is detected to fulfill one cardiovascular training target;
determining the training guidance attributes from said cardiovascular data with respect to the new cardiovascular training target of the physical exercise, wherein said determining includes whether the user is complying with the pre-defined cardiovascular training program;
selecting a basic video clip matching with the training guidance attributes; and
causing display of said basic video clip to the user.

10. The method of claim 1, wherein the training guidance attributes comprise at least one of increase training intensity, decrease training intensity, increase/decrease training intensity gradually, target heart rate, start exercise, stop exercise, start a next phase, start a next sub-phase, and an identifier of the next phase.

11. The method of claim 1, wherein determining the training guidance attributes from the cardiovascular data with respect to the at least one training target comprises determining a deviation from the pre-defined training program from said cardiovascular data, wherein said selecting a basic video clip comprises selecting, on the basis of the determined deviation, a basic video clip that deviates from the pre-defined training program.

12. The method of claim 1, wherein the at least one cardiovascular training target and the next cardiovascular training target define at least one of a target time and a target energy expenditure.

13. A computer program embodied on a non-transitory distribution medium readable by a computer and comprising program instructions which, when executed by an apparatus, perform operations comprising: acquiring, in a training guidance apparatus by using a heart rate sensor device, cardiovascular data representing cardiovascular measurement on a user carrying out a physical exercise associated with a pre-defined cardiovascular training program of the physical exercise, wherein the acquired cardiovascular data is real-time data measured by the heart rate sensor device during the physical exercise, and wherein the cardiovascular training program is defined by a plurality of cardiovascular training targets for the physical exercise; determining, in the training guidance apparatus on the basis of the acquired cardiovascular data and at least one of the plurality of cardiovascular training targets, cardiovascular performance associated with the user with respect to the cardiovascular training program during the exercise; determining, on the basis of the cardiovascular performance with respect to the cardiovascular training program, training guidance attributes for the physical exercise; selecting a basic video clip matching with the training guidance attributes; and causing display of said basic video clip to the user during the physical exercise; determining a need to instruct the user during said display of said basic video clip, and determining exercise guidance attributes describing the needed instruction; selecting an interrupt video clip matching with the determined exercise guidance attributes describing the needed instruction; causing interruption during the display of the basic video clip and displaying the interrupt video clip during the interruption; and upon determining, by the training guidance apparatus on the basis of the cardiovascular data with respect to the at least one of the plurality of cardiovascular training targets, that the user has fulfilled the at least one of the plurality of cardiovascular training targets, advancing the user to a next cardiovascular training target of the plurality of cardiovascular training targets different from the fulfilled at least one cardiovascular training target during the physical exercise, wherein the interruption during the display of the basic video clip causes the basic video clip and the interrupt video clip to be simultaneously displayed.

14. An apparatus comprising: at least one non-transitory memory storing computer program code; and at least one processing circuitry, wherein the processing circuitry, together with the at least one non-transitory memory and the computer program code, is configured to perform operations comprising: causing the apparatus by using a heart rate sensor device to acquire cardiovascular data representing cardiovascular measurement on a user carrying out a physical exercise associated with a pre-defined cardiovascular training program of the physical exercise, wherein the acquired cardiovascular data is real-time data measured during the physical exercise, and wherein the cardiovascular training program is defined by a plurality of cardiovascular training targets for the physical exercise; determining, in the at least one processing circuitry on the basis of the acquired cardiovascular data and at least one of the plurality of cardiovascular training targets, cardiovascular performance associated with the user with respect to the cardiovascular training program during the exercise; determining, on the basis of the cardiovascular performance with respect to the cardiovascular training program, training guidance attributes for the physical exercise; selecting a basic video clip matching with the determined training guidance attributes; causing display of said basic video clip to the user during the physical exercise; determining a need to instruct the user during said display of said basic video clip, and determining exercise guidance attributes describing the needed instruction; selecting an interrupt video clip matching with the determined exercise guidance attributes describing the needed instruction; causing interruption during the display of the basic video clip and displaying the interrupt video clip during the interruption; and upon determining, by the at least one processing circuitry on the basis of the cardiovascular data with respect to the at least one of the plurality of cardiovascular training target, that the user has fulfilled the at least one of the plurality of cardiovascular training targets, advancing the user to a next cardiovascular training target of the plurality of cardiovascular training targets different from the fulfilled at least one cardiovascular training target during the physical exercise, wherein the interruption during the display of the basic video clip causes the basic video clip and the interrupt video clip to be simultaneously displayed.

15. The apparatus of claim 14, wherein the operations further comprise providing a plurality of basic video clips, wherein each basic video clip is associated with metadata comprising the training guidance attributes.

16. The apparatus of claim 15, wherein the plurality of basic video clips is stored as video files in a standard video format.

17. The apparatus of claim 14, wherein the operations further comprise communicating over a logical connection with an exercise measurement device worn by the user and configured to measure cardiovascular data from the user, wherein the cardiovascular data is streamed from the exercise measurement device to the apparatus over the logical connection.

18. The apparatus of claim 17, wherein the logical connection is a network layer or a transport layer connection.

19. The apparatus of claim 17, wherein the operations further comprise connecting the logical connection through a public network between the apparatus and the exercise measurement device.

20. The apparatus of claim 14, wherein the operations further comprise:
   determining a training program comprising a plurality of training phases, each training phase associated with a basic video clip, wherein a plurality of basic video clips associated with said plurality of training phases is arranged in a determined order for display;
   providing training target parameters for each phase;
   monitoring said acquired cardiovascular data in relation to the training target parameters during each phase; and
   upon determining on the basis of said monitoring a need to instruct the user, determining exercise guidance attributes describing the needed instruction, selecting the interrupt video clip matching with the determined exercise guidance attributes describing the needed instruction, and causing interruption during the display of a basic video clip associated with current training phase and displaying the interrupt video clip during the interruption, and after the completion of the interrupt video clip, resuming the basic video clip.

21. The apparatus of claim 14, wherein the at least one cardiovascular training target and the next cardiovascular training target define at least one of a target time and a target energy expenditure.

22. A system comprising: a heart rate transmitter configured to acquire cardiovascular data representing cardiovascular measurement on a user carrying out a physical exercise associated with a pre-defined cardiovascular training program of the physical exercise, wherein the acquired cardiovascular data is real-time data measured during the physical exercise, and wherein the cardiovascular training program is defined by a plurality of cardiovascular training targets for the physical exercise; a storage configured to store a plurality of basic video clips, each basic video clip associated with metadata comprising exercise guidance attributes; and an apparatus, comprising at least one memory storing computer program code and at least one processing circuitry, wherein the processing circuitry, together with the at least one memory and the computer program code, is configured to perform operations comprising: causing the apparatus to acquire the cardiovascular data from the heart rate transmitter; determining, in the heart rate transmitter on the basis of the acquired cardiovascular data and at least one of the plurality of cardiovascular training targets, cardiovascular performance associated with the user with respect to the cardiovascular training program during the physical exercise; determining, on the basis of the cardiovascular performance with respect to the cardiovascular training program, training guidance attributes for the physical exercise; selecting a basic video clip matching with the determined training guidance attributes; causing display of said basic video clip to the user during the physical exercise; determining a need to instruct the user during said display of said basic video clip, and determining exercise guidance attributes describing the needed instruction; selecting an interrupt video clip matching with the determined exercise guidance attributes describing the needed instruction; causing interruption during the display of the basic video clip and displaying the interrupt video clip during the interruption; and upon determining, by the heart rate transmitter on the basis of the cardiovascular data with respect to the at least one of the plurality of cardiovascular training targets, that the user has fulfilled the at least one of the plurality of cardiovascular training targets, advancing the user to a next cardiovascular training target of the plurality of cardiovascular training targets different from the fulfilled at least one cardiovascular training target during the physical exercise, wherein the interruption during the display of the basic video clip causes the basic video clip and the interrupt video clip to be simultaneously displayed.

23. The system of claim 22, wherein the at least one cardiovascular training target and the next cardiovascular training target define at least one of a target time and a target energy expenditure.

* * * * *